United States Patent
Higgins et al.

(10) Patent No.: US 9,848,907 B2
(45) Date of Patent: *Dec. 26, 2017

(54) ROTATIONAL ATHERECTOMY DEVICE WITH BIASING CLUTCH

(71) Applicant: Cardiovascular Systems, Inc., St. Paul, MN (US)

(72) Inventors: Joseph Higgins, Minnetonka, MN (US); Jeffrey Allen McBroom, Champlin, MN (US)

(73) Assignee: Cardiovascular Systems, Inc., St. Paul, MN (US)

(*) Notice: Subject to any disclaimer, the term of this patent is extended or adjusted under 35 U.S.C. 154(b) by 532 days.

This patent is subject to a terminal disclaimer.

(21) Appl. No.: 14/208,713

(22) Filed: Mar. 13, 2014

(65) Prior Publication Data
US 2014/0316451 A1    Oct. 23, 2014

Related U.S. Application Data

(63) Continuation of application No. 14/208,478, filed on Mar. 13, 2014.
(Continued)

(51) Int. Cl.
*A61B 17/3207* (2006.01)
*F16D 3/10* (2006.01)
(Continued)

(52) U.S. Cl.
CPC ........ *A61B 17/320758* (2013.01); *F16D 3/10* (2013.01); *F16D 3/12* (2013.01);
(Continued)

(58) Field of Classification Search
CPC ... A61B 2090/031; F16D 7/025; F16D 3/005; F16D 7/002
See application file for complete search history.

(56) References Cited

U.S. PATENT DOCUMENTS 5,002,553 A    3/1991  Shiber
5,377,682 A    1/1995  Ueno et al.
(Continued)

OTHER PUBLICATIONS

International Preliminary Report on Patentability issued in PCT Application No. PCT/US2015/013171 and dated Aug. 11, 2016.

*Primary Examiner* — Katherine M Shi
*Assistant Examiner* — Michael Mendoza
(74) *Attorney, Agent, or Firm* — Barnes & Thornburg, LLP; Jeffrey R. Stone

(57) ABSTRACT

A rotational atherectomy system may include a drive shaft, a motor, and a clutch with a threshold torque where the clutch may include a motor plate rotationally connected to the motor, a drive shaft plate rotationally connected to the drive shaft, and a biasing clutch configured to rotationally engage the motor plate and the drive shaft plate, wherein torques less than the threshold torque are transmitted completely between the motor plate and the drive shaft plate, which remain rotationally coupled by static friction, and wherein torques greater than the threshold torque cause the motor plate and the drive shaft plate to rotate relative to one another and cause a residual torque to be transmitted between the motor and the drive shaft, the residual torque being less than the threshold torque and being determined by a kinetic coefficient of friction.

19 Claims, 17 Drawing Sheets

Related U.S. Application Data

(60) Provisional application No. 61/787,027, filed on Mar. 15, 2013, provisional application No. 61/932,409, filed on Jan. 28, 2014.

(51) Int. Cl.
*F16D 3/12* (2006.01)
*A61B 17/32* (2006.01)
*F16D 7/02* (2006.01)
*A61B 90/00* (2016.01)

(52) U.S. Cl.
CPC ............ *A61B 2017/320004* (2013.01); *A61B 2017/320766* (2013.01); *A61B 2090/031* (2016.02); *F16D 7/025* (2013.01)

(56) References Cited

U.S. PATENT DOCUMENTS

| | | |
|---|---|---|
| 5,695,506 A | 12/1997 | Pike et al. |
| 6,132,435 A | 10/2000 | Young |
| 6,257,351 B1 | 7/2001 | Ark et al. |
| 6,413,222 B1 * | 7/2002 | Pantages .............. A61B 8/12 600/466 |
| 6,454,717 B1 | 9/2002 | Pantages et al. |
| 6,517,528 B1 | 2/2003 | Pantages et al. |
| 6,758,818 B2 | 7/2004 | Pantages et al. |
| 7,025,151 B2 | 4/2006 | Hehli et al. |
| 7,950,560 B2 | 5/2011 | Zemlok et al. |
| 8,359,086 B2 | 1/2013 | Maschke |
| 2004/0147934 A1 | 7/2004 | Kiester |
| 2005/0274230 A1 | 12/2005 | Lin |
| 2007/0272269 A1 | 11/2007 | Wyatt et al. |
| 2008/0306339 A1 | 12/2008 | Hashimoto et al. |
| 2011/0004107 A1 | 1/2011 | Rosenthal et al. |
| 2011/0077673 A1 | 3/2011 | Grubac et al. |
| 2012/0239066 A1 | 9/2012 | Levine et al. |
| 2013/0048460 A1 | 2/2013 | Keller et al. |

\* cited by examiner

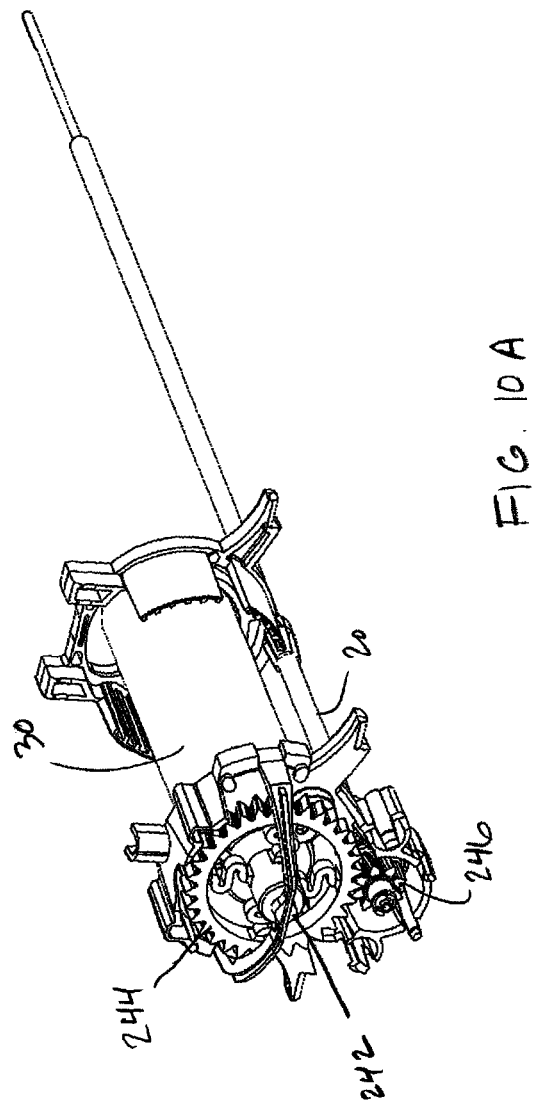

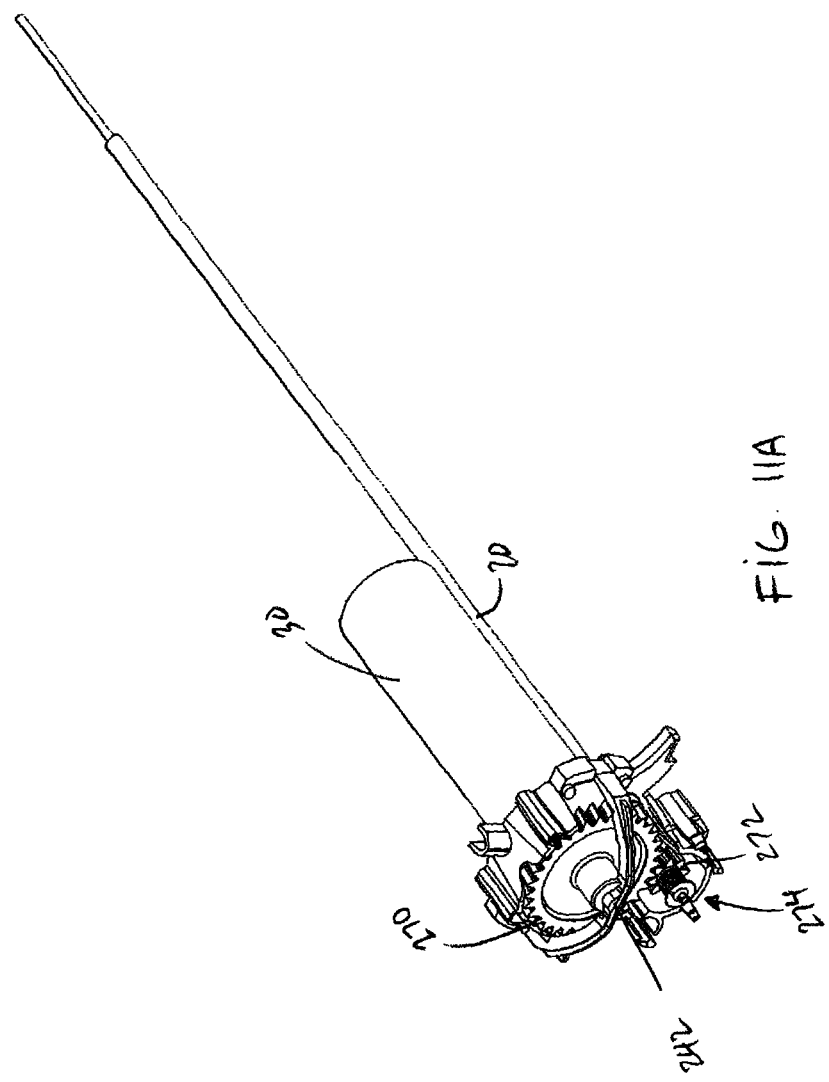

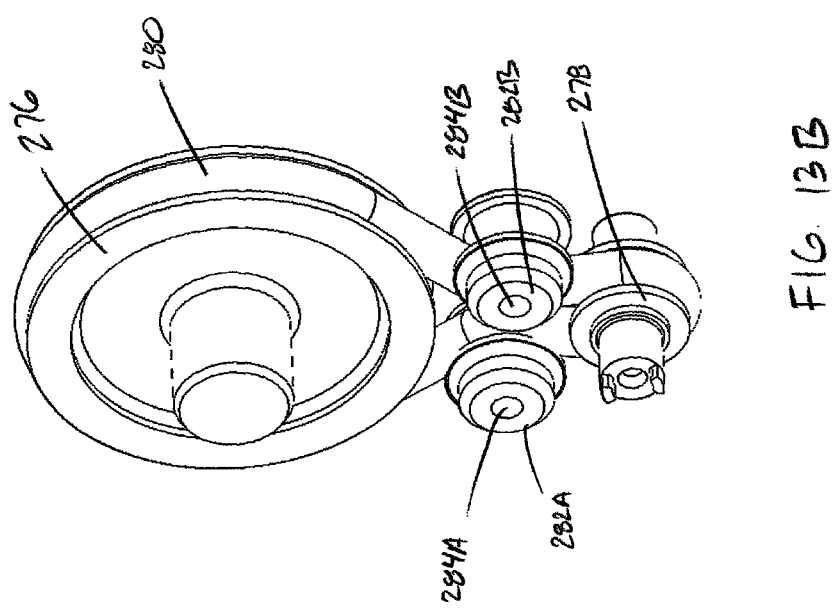

ROTATIONAL ATHERECTOMY DEVICE
WITH BIASING CLUTCH

CROSS-REFERENCE TO RELATED
APPLICATIONS

The present application is a continuation of U.S. patent application Ser. No. 14/208,478, entitled rotational atherectomy device with biasing clutch, filed Mar. 13, 2014 which claims priority to U.S. Provisional Patent Application 61/787,027 entitled rotational atherectomy device with biasing clutch, filed on Mar. 15, 2013, and claims priority to U.S. Provisional Patent Application 61/932,409 entitled devices, systems and methods for a shock absorbing drive system for medical devices, filed on Jan. 28, 2014, the contents of prior filed applications are hereby incorporated by reference herein in their entirety.

STATEMENT REGARDING FEDERALLY
SPONSORED RESEARCH OR DEVELOPMENT

Not Applicable

BACKGROUND OF THE INVENTION

Field of the Invention

The invention relates to devices and methods for removing tissue from body passageways, such as removal of atherosclerotic plaque from arteries, utilizing a rotational atherectomy device. In particular, the invention relates to improvements in a rotational atherectomy device having a biasing clutch and/or a shock absorbing element.

Description of the Related Art

Atherectomy is a non-surgical procedure to open blocked coronary arteries or vein grafts by using a device on the end of a catheter to cut or shave away atherosclerotic plaque (a deposit of fat and other substances that accumulate in the lining of the artery wall). For the purposes of this application, the term "abrading" is used to describe the grinding and/or scraping action of such an atherectomy head.

Atherectomy is performed to restore the flow of oxygen-rich blood to the heart, to relieve chest pain, and to prevent heart attacks. It may be done on patients with chest pain who have not responded to other medical therapy and on certain of those who are candidates for balloon angioplasty (a surgical procedure in which a balloon catheter is used to flatten plaque against an artery wall) or coronary artery bypass graft surgery. It is sometimes performed to remove plaque that has built up after a coronary artery bypass graft surgery.

Atherectomy uses a rotating shaver or other device placed on the distal end of a catheter to slice away or destroy plaque. At the beginning of the procedure, medications to control blood pressure, dilate the coronary arteries, and prevent blood clots are administered. The patient is awake but sedated. The catheter is inserted into an artery in the groin, leg, or arm, and threaded through the blood vessels into the blocked coronary artery. The cutting head is positioned against the plaque and activated, and the plaque is ground up or suctioned out.

The types of atherectomy are rotational, directional, and transluminal extraction. Rotational atherectomy uses a high speed rotating shaver to grind up plaque. Directional atherectomy was the first type approved, but is no longer commonly used; it scrapes plaque into an opening in one side of the catheter. Transluminal extraction coronary atherectomy uses a device that cuts plaque off vessel walls and vacuums it into a bottle. It is used to clear bypass grafts.

Performed in a cardiac catheterization lab, atherectomy is also called removal of plaque from the coronary arteries. It can be used instead of, or along with, balloon angioplasty.

Several devices have been disclosed that perform rotational atherectomy. For instance, U.S. Pat. No. 5,360,432, issued on Nov. 1, 1994 to Leonid Shturman, and titled "Abrasive drive shaft device for directional rotational atherectomy" discloses an abrasive drive shaft atherectomy device for removing stenotic tissue from an artery, and is incorporated by reference herein in its entirety. The device includes a rotational atherectomy apparatus having a flexible, elongated drive shaft having a central lumen and a segment, near its distal end, coated with an abrasive material to define an abrasive segment. At sufficiently high rotational speeds, the abrasive segment expands radially, and can sweep out an abrading diameter that is larger than its rest diameter. In this manner, the atherectomy device may remove a blockage that is larger than the catheter itself. Use of an expandable head is an improvement over atherectomy devices that use non-expandable heads; such non-expandable devices typically require removal of particular blockages in stages, with each stage using a differently-sized head.

U.S. Pat. No. 5,314,438 (Shturman) shows another atherectomy device having a rotatable drive shaft with a section of the drive shaft having an enlarged diameter, at least a segment of this enlarged diameter section being covered with an abrasive material to define an abrasive segment of the drive shaft. When rotated at high speeds, the abrasive segment is capable of removing stenotic tissue from an artery.

A typical atherectomy device includes a single-use disposable portion, which can be attached and detached from a non-disposable control unit (also referred to as a controller). The disposable portion includes elements that are exposed to saline and to the bodily fluids of the patient, such as a handle, a catheter, a rotatable drive shaft, and an abrasive head. The handle includes a turbine that rotates the drive shaft, and a knob that can longitudinally advance and retract the drive shaft along the catheter. Often, the device has a foot switch that activates the handle.

Typical known atherectomy devices use pneumatic power to drive the drive shaft, with the controller managing the amount of compressed air that is delivered to the turbine in the handle. The compressed air spins the turbine that, in turn, spins the drive shaft, and spins an abrasive crown attached to the drive shaft. Orbiting motion of the crown enlarges and widens the channel opening of a restricted or blocked vascular vessel.

There is currently a great deal of effort devoted to incorporating other types of rotational actuators into the atherectomy devices, primarily to replace the need for a source of compressed air. A motor requires a way limit the torque delivered to the drive shaft. For instance, if the distal end of the drive shaft encounters an obstacle and gets stuck (i.e., stops rotating), it is preferable that the torque delivered to the drive shaft be limited, so that the drive shaft does not wind up excessively and abruptly release. Such a sudden release of energy may result in damage to the patient or the device, and should be avoided.

Accordingly, there exists a need for a clutch between the motor and the drive shaft in a rotational atherectomy device.

BRIEF SUMMARY OF THE INVENTION

In some embodiments, a rotational atherectomy system may include an elongated, rotatable, flexible drive shaft having a distal end for insertion into a vasculature of a patient. The drive shaft may include a proximal end opposite the distal end that remains outside the vasculature of the patient. The system may include a motor for rotating the drive shaft and a shock absorbing element may be provided for coupling the motor to the drive shaft. During steady state conditions, the shock absorbing element may transfer the full torque from the motor to the drive shaft. However, during abrupt increases in the differential torque between the motor and the drive shaft, the shock absorbing element may absorb a portion of the increasing torque and, at the same time, may maintain a mechanical coupling between the drive shaft and the motor preventing slippage.

In other embodiments, a rotational atherectomy system may include a clutch having a characteristic threshold torque, comprising a motor plate rotationally connected to the motor, a drive shaft plate rotationally connected to the drive shaft, the motor plate and the drive shaft plate being parallel and coaxial, being disposed directly longitudinally adjacent to each other, and being held proximate one another longitudinally with a space therebetween, and a biasing clutch configured to rotationally engage the motor plate and the drive shaft plate.

While multiple embodiments are disclosed, still other embodiments of the present disclosure will become apparent to those skilled in the art from the following detailed description, which shows and describes illustrative embodiments of the invention. As will be realized, the various embodiments of the present disclosure are capable of modifications in various obvious aspects, all without departing from the spirit and scope of the present disclosure. Accordingly, the drawings and detailed description are to be regarded as illustrative in nature and not restrictive.

BRIEF DESCRIPTION OF THE SEVERAL VIEWS OF THE DRAWINGS

While the specification concludes with claims particularly pointing out and distinctly claiming the subject matter that is regarded as forming the various embodiments of the present disclosure, it is believed that the invention will be better understood from the following description taken in conjunction with the accompanying Figures, in which:

FIG. 10A shows a motor diagram of an atherectomy device having a shock absorbing drive gear, according to some embodiments.

FIG. 11A shows a motor diagram of an atherectomy device having a shock absorbing take-off element, according to some embodiments.

FIG. 13B shows a close-up view of the drive belt of FIG. 12A, according to some embodiments.

DETAILED DESCRIPTION OF THE INVENTION

An atherectomy device is disclosed, with a clutch between the motor and the drive shaft. The clutch may include two plates that rely on friction to transmit torque from one plate to the other. The clutch may have an attractive magnetic normal force that holds the plates together or, in another embodiment, a biasing mechanism may hold the plates together. For relatively low torques, as is the case during normal use, a static frictional torque may holds the plates together, and the plates spin together without slipping. For relatively high torques, as occurs when the distal end of the drive shaft encounters an obstacle and stops abruptly, the high torque exceeds the maximum possible static frictional torque, and the plates slip. When slipping, the plates transmit a kinetic frictional torque that is low enough to avoid damage to the patient or to the atherectomy device. In some cases, the torque levels associated with a stoppage of the drive shaft distal end are chosen to mimic those of a known atherectomy device, in which a gas-driven turbine is clutchlessly attached to the drive shaft. In other embodiments, rather than a frictional force being used to transmit the torque, a biasing mechanism having variable torsional strength may be used to transfer the torque. For example, a spring may connect the clutch plates and may transfer the torque based on a torsional stiffness of the spring. When an obstruction is encountered, the variable torsional stiffness may allow the spring to wind and may allow for delay in an excessive torque at the distal end being applied. As such, the biasing mechanism in this embodiment may allow for a speed or current interrupter to cause the drive shaft to stop, for example.

The preceding paragraph is merely a summary, and should not be construed as limiting in any way. A more detailed description of the several embodiments follows.

Figure 1:
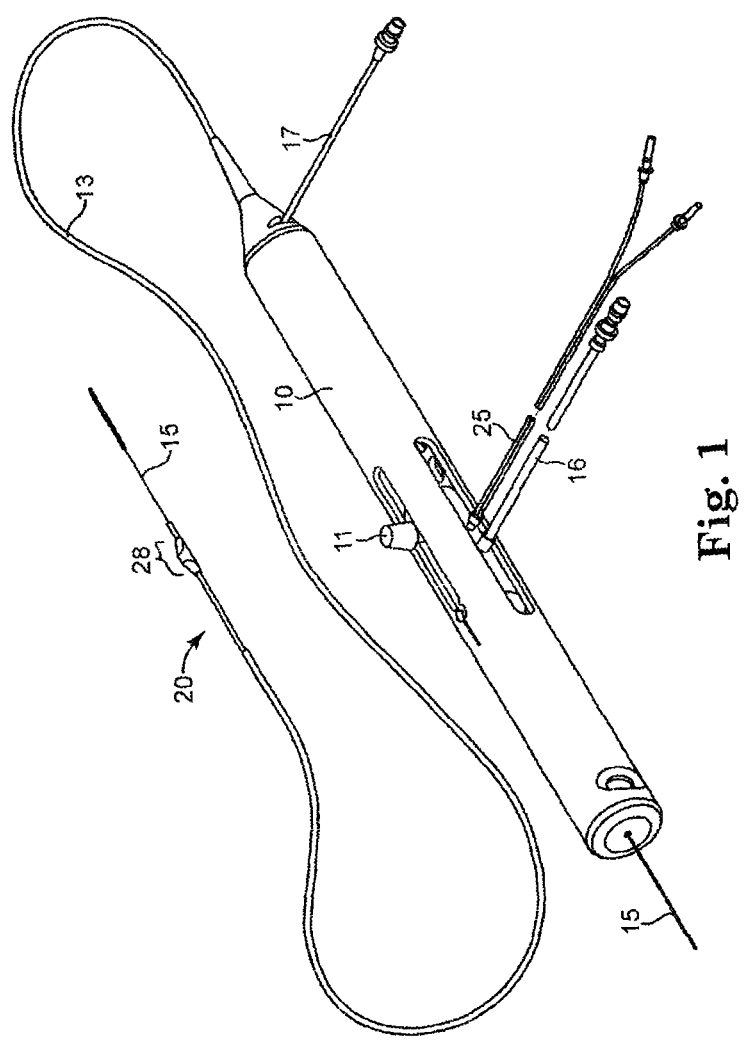
FIG. 1 is a perspective view of a known rotational atherectomy device.

FIG. 1 is a schematic drawing of a typical rotational atherectomy device. The device includes a handle portion 10, an elongated, flexible drive shaft 20 having an eccentric enlarged abrading head 28, and an elongated catheter 13 extending distally from the handle portion 10. The drive shaft 20 is constructed from helically coiled wire as is known in the art and the abrading head 28 is fixedly attached thereto. The catheter 13 has a lumen in which most of the length of the drive shaft 20 is disposed, except for the enlarged abrading head 28 and a short section distal to the enlarged abrading head 28. The drive shaft 20 also contains an inner lumen, permitting the drive shaft 20 to be advanced and rotated over a guide wire 15. A fluid supply line 17 may be provided for introducing a cooling and lubricating solution (typically saline or another biocompatible fluid) into the catheter 13.

The handle 10 desirably contains a turbine (or similar rotational drive mechanism) for rotating the drive shaft 20 at high speeds. The handle 10 typically may be connected to a power source, such as compressed air delivered through a tube 16. A pair of fiber optic cables 25, alternatively a single fiber optic cable may be used, may also be provided for monitoring the speed of rotation of the turbine and drive shaft 20. Details regarding such handles and associated instrumentation are well known in the industry, and are described, e.g., in U.S. Pat. No. 5,314,407, issued to Auth, and incorporated by reference herein in its entirety. The handle 10 also desirably includes a control knob 11 for advancing and retracting the turbine and drive shaft 20 with respect to the catheter 13 and the body of the handle.

The abrasive element 28 in FIG. 1 is an eccentric solid crown, attached to the drive shaft 20 near the distal end of the drive shaft 20. The term "eccentric" is used herein to denote that the center of mass of the crown is laterally displaced away from the rotational axis of the drive shaft 20. As the drive shaft rotates rapidly, the displaced center of mass of the crown causes the drive shaft to flex radially outward in the vicinity of the crown as it spins, so that the crown may abrade over a larger diameter than its own rest diameter. Eccentric solid crowns are disclosed in detail in, for example, U.S. patent application Ser. No. 11/761,128, filed on Jun. 11, 2007 to Thatcher et al. under the title, "Eccentric abrading head for high-speed rotational atherectomy devices", published on Dec. 11, 2008 as U.S. Patent Application Publication No. US2008/0306498, and incorporated by reference herein in its entirety.

There is currently an effort to replace the gas-driven turbine of the known atherectomy device with an electric motor. Such a motor has different mechanical characteristics than the turbine, such as an increased rotational inertia. The present application is directed mainly to a clutch that connects a motor to the drive shaft. Such a clutch can limit the torque delivered by the motor, so that if the distal end of the drive shaft encounters an obstacle and suddenly stops rotating, the clutch will prevent a damaging amount of torque from being delivered to the drive shaft. Aside from the motor, many or all of the other elements of the known atherectomy device of FIG. 1 may be used with the present disclosed head design, including the catheter 13, the guide wire 15, the control knob 11 on the handle 10, the helically coiled drive shaft 20 and the eccentric solid crown 28.

Figure 2:
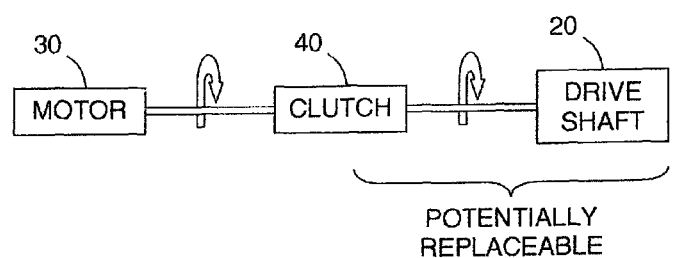
FIG. 2 is a block diagram of the motor, the drive shaft and the clutch that mechanically couples them together.

FIG. 2 is a block diagram of the motor 30, the drive shaft 20 and the clutch 40 that mechanically couples them together. In this figure and those that follow, the "motor" may be an electric motor, a gas-driven turbine, or any suitable device that generates a controllable amount of rotation. During normal use, the clutch 40 is engaged, and the rotation produced by the motor 30 is passed directly on to the drive shaft 20. In the event that the distal end of the drive shaft 20 becomes caught or encounters a blockage that suddenly stops its rotation, the clutch disengages, so that the motor 30 does not continue to rotate the proximal end of the drive shaft. Such a continued rotation would excessively wind up the drive shaft, and the torques associated with such a winding could potentially damage the blood vessel of the patient or the atherectomy device itself, which are both undesirable outcomes.

Additionally, the clutch may provide a convenient interface between the drive shaft, which is typically a replaceable or disposable element, and the motor, which is typically used repeatedly.

Figure 3:
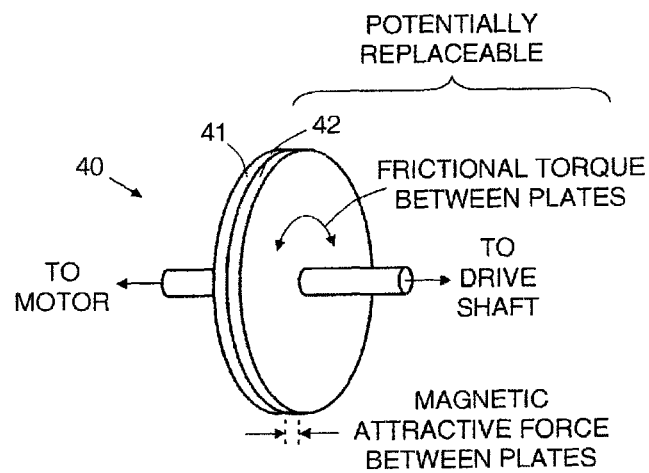
FIG. 3 is a schematic drawing of the clutch of FIG. 2.

FIG. 3 is a schematic drawing of the clutch 40 of FIG. 2. The clutch 40 includes two plates, 41 and 42, held together by an attractive magnetic force. The plates 41, 42 are attached to spindles that rotationally couple them to the motor 30 and drive shaft 20, respectively.

During normal operation, including spin-up, constant rotational speeds, and spin-down, the difference in torque between the motor and the proximal end of the drive shaft is relatively small. For these small torque differences, the magnetic attractive force is sufficient to hold the plates 41 and 42 together, and the proximal end of the drive shaft is spun along with the motor.

If the distal end of the drive shaft encounters an obstacle and is suddenly stopped from rotating, the torque difference between the motor and the proximal end of the drive shaft increases rapidly and eventually exceeds the static frictional torque that holds the plates together. When this happens, the plates slip rotationally with respect to each other, and transmit a kinetic frictional torque from one to the other as they slip. A detailed discussion of these frictional effects follows below.

Note that torque is the rotational analog of the quantity, force. Torque produces a change in angular momentum, much like linear force produces a change in linear momentum. Because the rotational inertia of the device components remains roughly constant throughout their operation, a non-zero torque therefore produces a change in rotational speed.

Note also that the two plates 41 and 42, which are held together magnetically, may provide a convenient interface for replacement. For instance, after a procedure has been performed, the drive shaft and associated mechanical parts may be removed by detaching the magnetically-attracted plates 41 and 42. Plate 42 is disposed of, along with the drive shaft, while plate 41 remains with the motor unit and may be used repeatedly.

Figure 4:
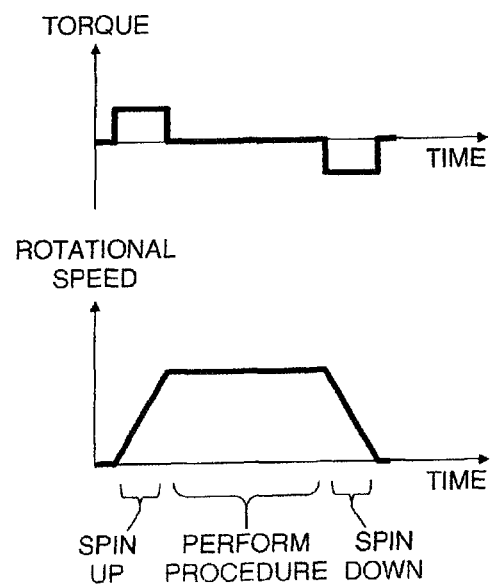
FIG. 4 is a plot of rotational speed of the drive shaft and torque at the distal end of the drive shaft, for a typical procedure.

FIG. 4 is a plot of rotational speed of the drive shaft and torque at the distal end of the drive shaft, for a typical procedure. Initially, the drive shaft is at rest and there are no net torques present. During the "spin-up" phase, the motor applies a non-zero torque to the proximal end of the drive shaft, and the rotational speed of the drive shaft increases. Once a desired rotational speed is reached, the torque of the motor is reduced to keep the drive shaft at a constant rotational speed. Note that the actual torque applied by the motor to the proximal end of the drive shaft may be small but non-zero, in order to overcome the effects of friction between the proximal and distal ends of the drive shaft. The plot shows the torque at the distal end of the drive shaft, which is truly zero when the distal end of the drive shaft rotates at a constant rotational speed. During the "spin-down" phase, the motor applies a non-zero torque in the opposite direction to reduce the rotational speed of the drive shaft to zero.

The typical torque levels shown in FIG. 4, which commonly occur during use, are usually below a threshold at which the plates 41, 42 in the clutch 40 begin to slip. During normal use, the clutch remains engaged, and the static frictional force between the plates holds the plates together. It is desired that the plates slip, and the clutch disengages, only during an atypical event, such as when the distal end of the drive shaft becomes stuck and stops rotating. However, it is possible that the plates may slip during spin-up and/or spin-down, due to the spin-up and/or spin-down torques exceeding the threshold.

At this point, it is instructive to review the physics of frictional forces, in order to better understand when the clutch plates hold together, and when they slip.

Consider for a moment two linear plates, rather than two rotating plates as in the true clutch of FIG. 3. The linear plates are held together by a normal force that can be generated magnetically, as is the case of the clutch of FIG. 3, or can be generated externally. For relatively small forces parallel to the contact surfaces, the plates hold together. In other words, if one pushes gently on one plate, parallel to the contact surfaces, the other plate holds with it and there is no slippage. For relatively large forces parallel to the contact surface, such as a strike with a hammer, the plates no longer hold together, and slip past each other along the contact surface.

The threshold at which slippage begins to occur is given by the product of the normal force (i.e., the force holding the plates together, generated magnetically or otherwise) and a coefficient of static friction. The coefficient of static friction is a dimensionless quantity that is typically less than one. For forces less than this threshold, the plates hold together. For forces greater than this threshold, the plates slip.

As an example, consider the interface between a rubber tire and a road surface. For a small normal force, as is the case when the tire is simply resting on the road under the effects of its own gravitational weight, it is easy to drag the tire along the road surface. For a large normal force, as is the case when the tire supports the weight of a car, it is quite difficult to overcome the frictional forces that keep the tire in contact with the road. In practice, skidding only occurs for large forces, such as slamming on the brakes during driving conditions.

From this example, we may state a first general principle for our clutch: the normal force (i.e., the magnetically-generated force that attracts the plates to each other) determines the threshold at which slipping between the plates begins to occur.

Such a normal force is controllable at the design phase of the clutch, and may be controlled by the lateral distribution of magnetic materials in the plates, as well as the longitudinal distribution of those materials. For instance, the normal force decreases as the longitudinal spacing between the magnetic particles increases; such spacing can be achieved in many ways, such as by coating the magnetic particles with a non-magnetic layer.

Returning to the example of the two linear plates, consider now the case when the plates are already slipping past each other. There is a resisting force generated at the contact surfaces, which would slow down and eventually stop the slipping motion, if no other forces were at work. Likewise, if one were to push of the sliding plates parallel to the surfaces with a force equal to the resisting force, there would be no net forces on the plates and the plates would maintain a constant velocity between them.

The resisting force is equal to the product of the normal force and a coefficient of kinetic friction. The coefficient of kinetic friction is also a dimensionless quantity, also typically less than one. Furthermore, the coefficient of kinetic friction is usually less than the coefficient of static friction; this is the reason behind the effectiveness of automotive anti-lock brakes, which can impart a greater stopping force if there is no skidding involved.

Importantly, the resisting force does not depend on the velocity between the plates; as long as there is slipping between the plates, the resisting force depends only on the normal force between the plates.

We may state a second general principle for our clutch: the normal force (i.e., the magnetically-generated force that attracts the plates to each other) determines the torque transmitted from one plate to the other when the plates are slipping.

Figure 5:
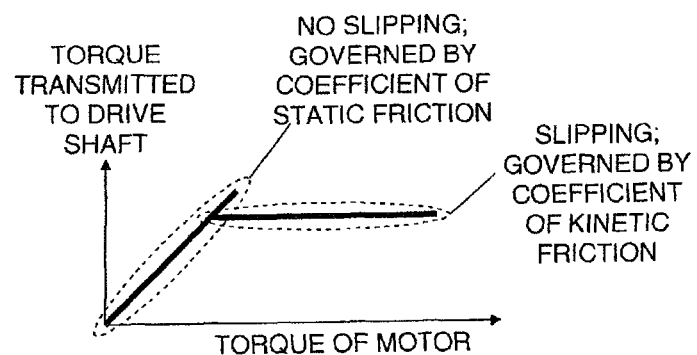
FIG. 5 is a plot of the torque transmitted to the proximal end of the drive shaft, versus the torque of the motor.

These two general principles are summarized in FIG. 5, which is a plot of the torque transmitted to the proximal end of the drive shaft (vertical axis), versus the torque of the motor (horizontal axis).

If there were no clutch present, and the drive shaft were rotationally attached directly to the motor, the "no slipping" curve in FIG. 5 would increase from the origin to the upper right edge of the plot in a 1:1 relationship. In other words, for a clutchless attachment, all of the motor torque is always transmitted to the drive shaft.

At relatively low torques, at which the clutch is engaged and the plates are in contact and do not slip with respect to each other, the 1:1 relationship is seen. In normal use, such as during the spin-up and spin-down portions of the atherectomy cycle, the torques produces by the motor are considered relatively low, so that the clutch remains engaged throughout the procedure. On the plot in FIG. 5, this corresponds to the 45-degree branch extending to the right and upward from the origin (labeled "no slipping").

At some particular torque threshold, we want slipping to start, in order to prevent damage to the patient and to the device itself. This threshold occurs at the top-right point of the "no slipping" curve, and is proportional to the normal force. Slipping occurs when the torque of the motor equals or exceeds this threshold value.

When there is slipping between the plates in the clutch, the torque that is transmitted to the drive shaft cannot exceed a particular "slipping" value, regardless of how large the actual torque of the motor is. This limits the maximum torque that can be transmitted to the drive shaft, which also prevents damage to the patient and to the device itself. This "slipping" torque value is also proportional to the normal force, and may be referred to herein as a "residual" torque.

Note that because the kinetic coefficient of friction is generally less than the static coefficient of friction, the two curves intersect as shown in FIG. 5, with the "no slipping" portion extending upward at to the right, beyond the intersection point.

In general, the curves in FIG. 5 are scalable in proportion to the normal force. If the normal force is doubled, for example, the "no slipping" curve extends twice as far to the top-right, and the "slipping" torque value is doubled. The normal force is controllable during the design phase of the clutch, through the choice of magnetic materials in the plates and the lateral and longitudinal placement of those materials.

Figure 6:
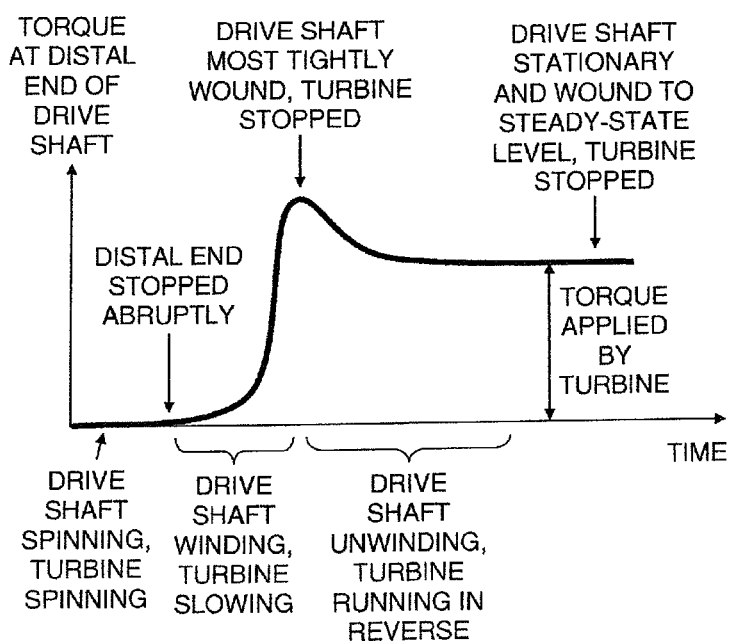
FIG. 6 is a plot of torque at the distal end of the drive shaft versus time for a distal-end-stopping event, for a known gas turbine system.
Figure 7:
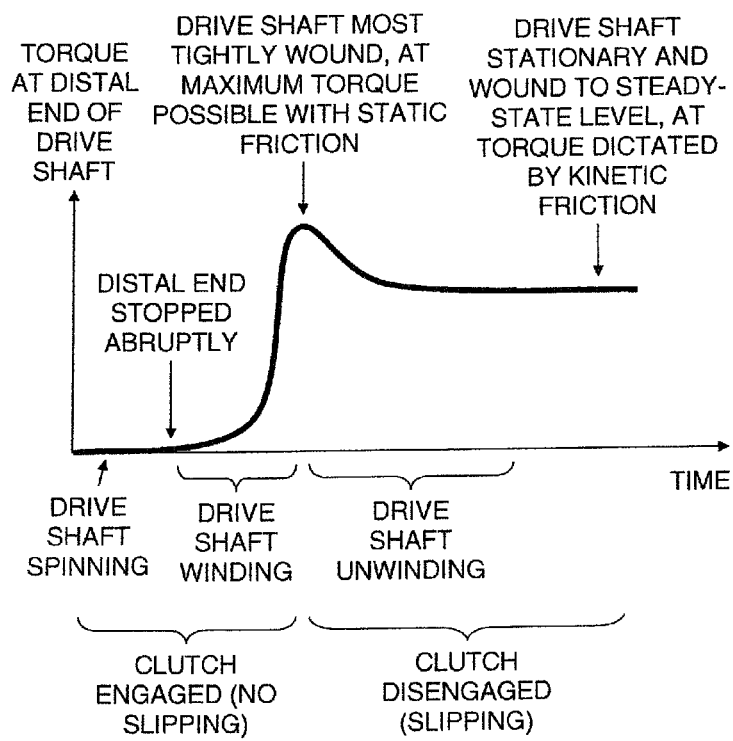
FIG. 7 is a plot of torque at the distal end of the drive shaft versus time for a distal-end-stopping event, for the present motor-driven system with the clutch of FIG. 3.

The curves of FIG. 5 are plotted as torque versus torque. In order to see how these torques evolve in time when the distal end of the drive shaft is abruptly stopped, two examples are presented in FIGS. 6 and 7. FIG. 6 pertains to a known system, in which the drive shaft is connected to a gas turbine, and does not use a clutch. The rotational inertia of the gas turbine is small enough so that the associated torques do not cause any damage to the patient or to the device. FIG. 7 pertains to a system that uses a higher-rotational-inertia motor, such as an electric motor, which uses the clutch to prevent damage. In particular, the peak and steady-state torque values in FIG. 7 are chosen to mimic those in FIG. 6, which have been determined to be acceptable in practice.

We first turn to FIG. 6, which is a plot of torque at the distal end of the drive shaft versus time for a distal-end-stopping event, for a known gas turbine system. The known gas turbine system does not have a clutch.

Initially, both the motor and drive shaft are spinning together. The rotation is assumed to be at a constant rotational speed, so there is no net torque on the distal end of the drive shaft.

Next, the distal end of the drive shaft is stopped abruptly, as would happen if it got stuck or encountered an obstacle in the blood vessel.

Following the abrupt stop, the drive shaft begins to wind up, or rotationally compress. Such a compression is analogous to a linear spring; the more it is compressed, the harder it becomes to impart additional compression. In this phase, the drive shaft essentially "pushes back" rotationally on the motor, and the motor slows down.

There comes a point when all the rotational energy has gone into rotationally compressing the spring, and the spring and motor are stopped at the spring's maximum compression point. At this point, the distal end of the drive shaft experiences its maximum torque.

Following the maximum compression, the drive shaft "springs back" and unwinds a bit. During this unwinding, the motor and the proximal end of the drive shaft run in reverse. In practice, there may be some "ringing" to this curve, as the energy in the system oscillates between kinetic (movement) and potential (rotational compression of the drive shaft). Much of the "ringing" is damped due to friction, and the oscillations become increasingly small as system settles to a stationary steady state. The "ringing" is omitted from FIG. 6.

At this steady state, the motor is stopped but is still applying a torque. The drive shaft is also stationary, but is stationary in a rotationally compressed position due to the motor torque.

The entire horizontal axis of FIG. 6 may last on the order of milliseconds. The known gas turbine may have a control system that detects when its rotational speed falls below a threshold value or falls to zero and subsequently shuts off the motor. Such a control system may require a particular length of time to react, typically on the order of several seconds. These control systems cannot react directly to portions of the curve of FIG. 6, though, because the spike and settling to steady-state typically occurs much more rapidly than the control system can react.

There are two torque values to note on the curve of FIG. 6. The first value is the peak value, which occurs when the drive shaft is most tightly wound and the motor is stopped. The second value is the steady-state value. Both of these torque values have been deemed safe for use in the known, gas turbine-driven atherectomy system. As a result, the clutch 40 may be designed to mimic one or both of these safe torque values.

FIG. 7 is a plot of torque at the distal end of the drive shaft versus time for a distal-end-stopping event, for the present motor-driven system with the clutch of FIG. 3. One difference between FIGS. 6 and 7 is that for the present clutch design, the motor continues to turn throughout the clutch disengagement; for the known gas turbine of FIG. 6, the turbine stops along with the drive shaft. Such a stopping of the present motor is not feasible because of the relatively large rotational inertia of the motor.

Initially, both the motor and drive shaft are spinning together. The rotation is assumed to be at a constant rotational speed, so there is no net torque on the distal end of the drive shaft. The clutch is engaged, and there is no slipping between the plates of the clutch.

Next, the distal end of the drive shaft is stopped abruptly. As with FIG. 6, the spiked torque associated with stopping the distal end is omitted from FIG. 7.

Following the abrupt stop, the drive shaft begins to wind up, or rotationally compress. In this phase, the drive shaft essentially "pushes back" rotationally on the motor, and the motor may slow down. In practice, this slowing down of the motor may be very slight, because the rotational inertia of the motor may be quite large, especially compared with that of the gas turbine discussed above.

Eventually, as the distal end of the drive shaft remains fixed and the proximal end of the drive shaft continues to wind, there will reach a point when the torque difference between the motor and the proximal end of the drive shaft equals the threshold torque, beyond which the clutch plates start to slip. This threshold point corresponds to the peak of the curve in FIG. 7.

One may trace the progress thus far in FIG. 5. Initially, while the motor and drive shaft are spinning together, the system as at the origin. After the distal end is stopped, the system rises upward and to the right along the "no slipping" curve. The threshold point, which is the peak of the curve in FIG. 7, is at the top-right-most edge of the "no slipping" curve in FIG. 5.

Once the plates begin to slip, the clutch becomes disengaged. The motor continues to rotate, along with plate 41 of the clutch 40. The other plate 42, however, rotates more slowly than the plate 41, and eventually stops and unwinds, along with the proximal end of the drive shaft. Once any ringing effects have died off and steady state is reached, the drive shaft is stationary and slightly wound, the proximal end of the drive shaft is stationary, the plate 42 is stationary, the plate 41 remains rotating along with the motor, and rotating plate 41 transmits enough torque to stationary plate 42 to keep the drive shaft slightly wound.

Essentially, the torque transmitted by the clutch 40 in its slipping mode is analogous to the torque of the gas turbine of FIG. 6 when the gas turbine is stationary. In fact, during the design phase of the clutch 40, the attractive magnetic normal force between the plates can be set so that the steady-state torque of FIG. 7 matches that of FIG. 6, since the steady-state torque of the gas turbine has been deemed safe for use. Alternatively, the attractive magnetic normal force between the plates can be set so that the peak torque, i.e., the threshold torque value at which the plates begin to slip (the peak in FIG. 7), matches that of FIG. 6. As a further alternative, both the peak and steady-state torque values can be met by texturing one or both surfaces of the clutch, adjusting the diameter of the contact surfaces, and/or adjusting the materials on the opposing faces in the clutch.

Although the plates 41 and 42 are drawn in FIG. 3 as being coaxial and circular, other suitable shapes and orientations may be used. One or both surfaces may optionally be textured, which can adjust the surface area in contact and may affect the frictional performance of the interface. In addition, the plates 41 and 42 may optionally be curved, and may have mating curvatures that fit together. For instance, one plate may be convex with a particular radius of curvature, and the other plate may be concave with the same radius of curvature.

Figure 8A:
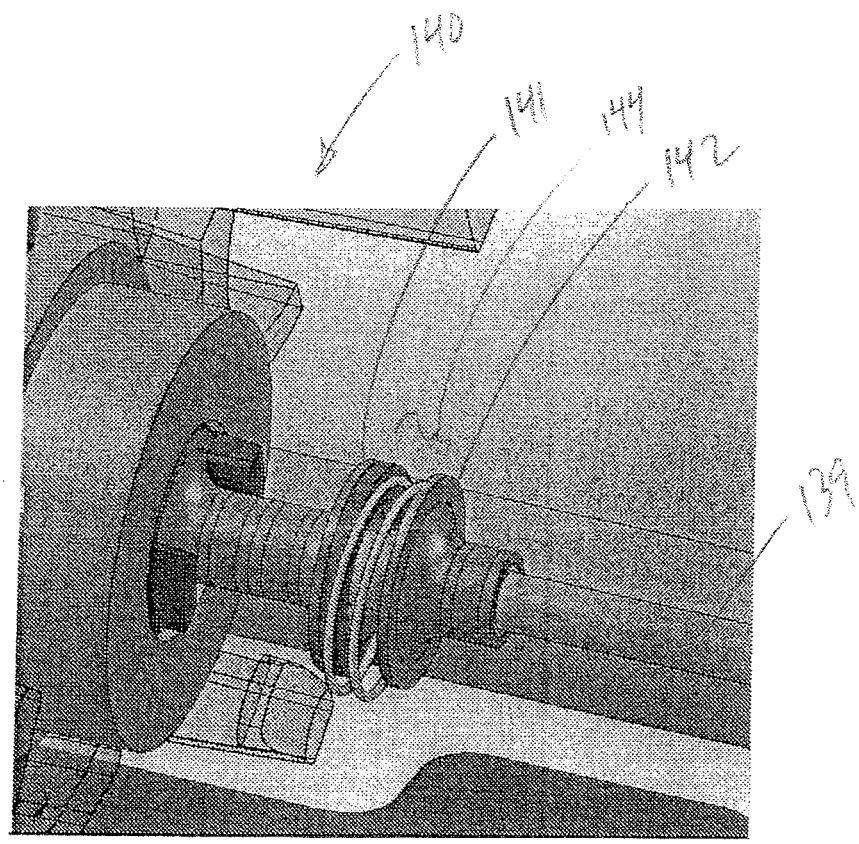
FIG. 8A shows a biasing clutch according to some embodiments.

Referring now to FIG. 8A, an additional embodiment of a clutch 140 is shown. In this embodiment, a clutch 140 is formed by a boundary element 141 formed by a pair of loft flanges secured to one another and rotationally coupled (e.g., keyed) to the motor. The clutch may also include a boundary element 142 formed by another loft flange secured to a tube 139, such as a hypotube that is used to rotate the drive shaft. As shown, a biasing mechanism 144 may be arranged between the boundary elements 141, 142 to transfer the torque from the motor to the drive shaft via the boundary elements 141, 142. It is to be appreciated that, while the boundary elements 141, 142 have been described as loft flanges, these elements may take other forms such as disc-shaped plates, square plates, hollow or solid cylindrical cylinders, or other shaped boundary elements 141, 142 may be provided.

Figure 8B:
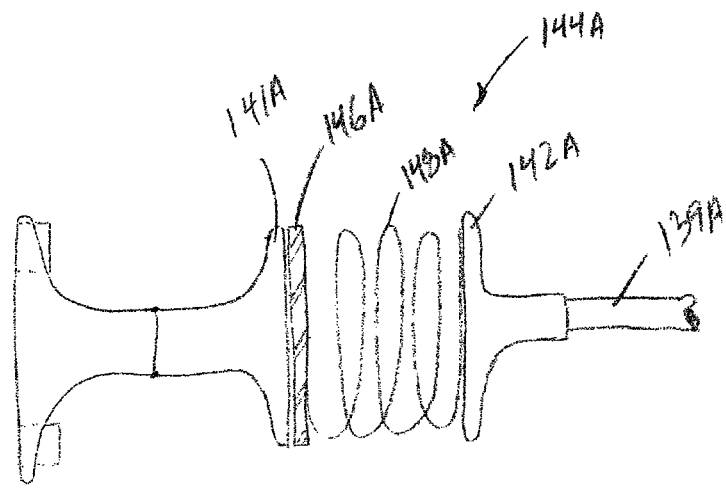
FIG. 8B shows a schematic diagram of one embodiment of the biasing clutch of FIG. 8A.

Referring now to FIG. 8B, a schematic diagram of a first biasing mechanism 144A is shown. In this embodiment, the function of the clutch 140 may be very similar to that of the magnetic clutch 40 previously described. That is, a spring 148A or other biasing mechanism 144A may extend from one of the faces of one of the loft flanges 142A and a plate 146A may be provided on one end of the spring 148A opposite the flange 142A that the spring 148A is attached to. The plate 146A may frictionally engage the faces of the opposing loft flange 141A. The spring 148A may have a relaxed length longer than the distance between the loft flanges 141A, 142A and, as such, the spring 148A may be compressed to fit within the loft flanges 141A, 142A thereby creating a longitudinal normal force that presses the plate 146A against the loft flange 141A. Like the magnetic clutch described, the friction between the plate 146A and the loft flange 141A may be sufficient to support transfer of a threshold torque between the plates, but when the threshold torque is exceeded (e.g., when the drive shaft hits an obstruction) the plate 146A and the loft flange 141A may slip thereby reducing the torque transfer to a torque based on kinetic friction in lieu of static friction. It is noted, however, that in addition to the slippage of the plate 146A and the loft flange 141A the use of a spring 148A to bias the plate may provide some amount of additional torsional play in the system. As such, when the drive shaft hits an obstruction, in some embodiments, the torsional stiffness of the spring 148A may result in some relative rotation of the hypotube and motor prior to the slippage of the frictional surface. It is to be appreciated that while the spring 148A is shown as being attached to the loft flange 142A on the hypotube 139A and the plate 146A is shown to frictionally engage the loft flange 141A coupled to the motor, the reverse may also be provided.

Figure 8C:
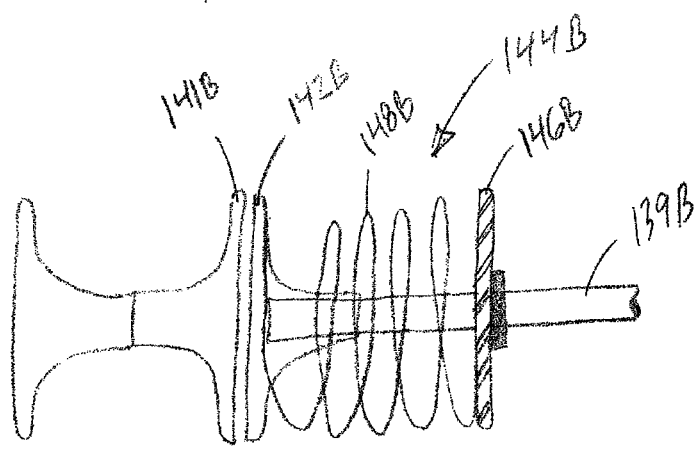
FIG. 8C shows a schematic diagram of another embodiment of the biasing clutch of FIG. 8A.

Referring now to FIG. 8C, a schematic diagram of a second biasing mechanism 144B is shown. In this embodiment, the function of the clutch 140 may remain similar to that of the magnetic clutch. In this embodiment, rather than placing the spring 148B and plate 146B between the loft flanges 141B, 142B, the plate 146B may be positioned on the tube 139B and secured to prevent longitudinal movement of the plate 146B relative to the tube 139B. The loft flange 142B on the tube 139B may be longitudinally slidable, but rotationally coupled to the hypotube 139B through a key or square drive fitting or other relative rotation resisting connection. Like the embodiment of FIG. 8B, a spring 148B may be provided that has a relaxed length longer than the space available in the system. As such, the spring 148B may be compressed between the plate 146B and a loft flange on the hypotube 139B thereby biasing the loft flange 142B on the tube 139B against the loft flange 141B coupled to the motor and creating a friction based torque transferring connection. This embodiment may also be reversed by placing the plate 146B and spring 148B on the motor side of the clutch, for example. Like the embodiment of FIG. 8B a threshold torque may be supported, but may be overcome if an obstruction is encountered. However, unlike the embodiment of FIG. 8B, since the spring 148B is not carrying torque in this embodiment, play provided in FIG. 8B may not be available. However, it is appreciate that the plate 146B and spring 148B may be rotationally coupled to the tube 139B and the loft flange 142B on the tube 139B may be positioned on the tube 139B to allow for both rotational and longitudinal movement such that the spring 148B transfers the torque to the loft flange 142B. In this latter situation the play from the spring 148B may be provided.

Figure 8D:
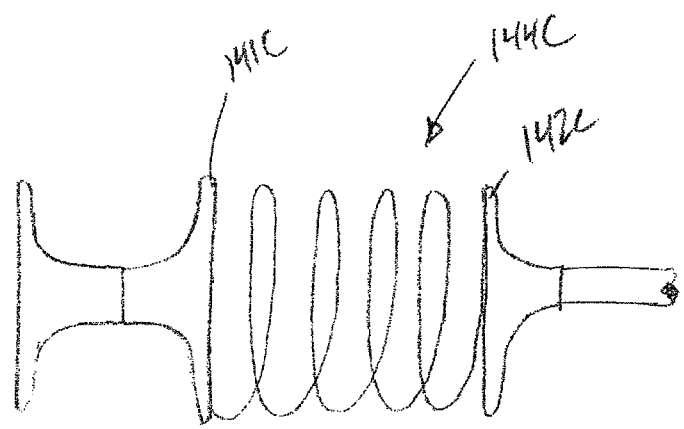
FIG. 8D shows a schematic diagram of another embodiment of the biasing clutch of FIG. 8A.

Referring now to FIG. 8D, a schematic diagram of yet another biasing mechanism 144C is shown. In this embodiment, the two boundary elements 141C, 142C of the clutch may be directly secured to one another with a biasing mechanism 144C such as a spring 148C, for example. The spring 148C may have a relaxed length equal to, larger, or smaller than the space provided between the loft flanges 141C, 142C. When in place, the spring 144C may have a torsional resistance that may change based on how tightly wound the spring 148C is. As such, upon actuation of the drive shaft, the spring 148C may wind up tighter until equilibrium is found between the torque required to rotate the drive shaft and the torsional resistance supplied by the spring 148C. In this embodiment, when an obstruction is encountered, the added torque applied to the spring 148C may cause the spring 148C to further wind allowing the loft flanges 141C, 142C of the clutch to rotate relative to one another and, thus, not fully transfer the torque from the motor. In this embodiment, since no slippage is provided by the clutch, the system may be further equipped with a speed or current limiting switch for switching off the motor when an obstruction is encountered. However, at initial impact between the distal end of the drive shaft and the obstruction, the clutch may allow for some play in the system and avoid relatively high torques from being realized. Systems for releasing the torque provided by the motor based on torque, current, voltage, speed reduction and the like are discussed in U.S. patent application Ser. No. 12/713,558, the contents of which are hereby incorporated by reference herein in their entireties.

Figure 9A:
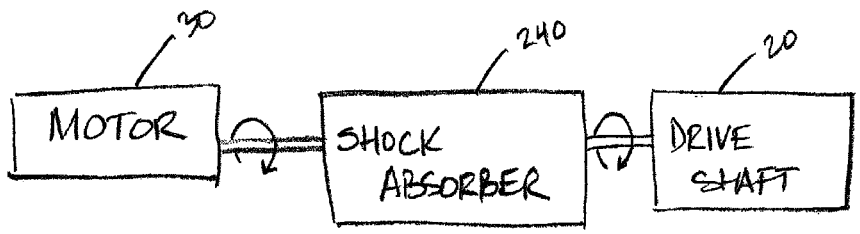
FIG. 9A shows a block diagram of a motor, a drive shaft, and a shock absorbing element that mechanically couples them together.

Referring now to FIG. 9A, a block diagram and torque graph are shown that may reflect the embodiment of FIG. 8D. That is, in the embodiment of FIG. 8D, for example, a slipping type clutch is not provided and, instead, a shock absorbing spring 144C is provided to elastically couple the motor 30 to the drive shaft 20. The block diagram of FIG. 9A shows this in a block form indicating that as the motor 30 spins a first direction, the shock absorbing element 240 may directly transfer the torque to the drive shaft 20. That is, at initial startup, for example, the shock absorbing element 240 may elastically stretch or compress or deform in shear by an initial amount until the elasticity of the shock absorber finds equilibrium with the torsional friction/resistance being encountered by the drive shaft 20. Beyond that point, aside from situations where the torsional resistance witnessed by the drive shaft 20 varies, the motor 30, the shock absorber 240, and the drive shaft 20 may rotate at a state of equilibrium where the rotational speeds differ by any gearing changes, but otherwise remain consistent.

Figure 9B:
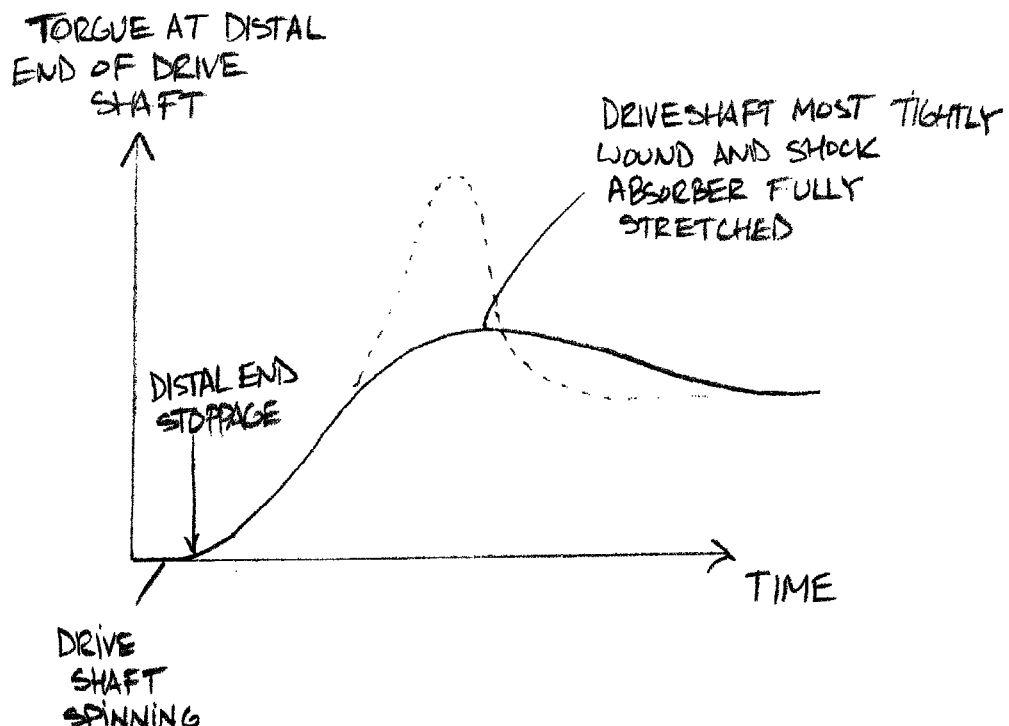
FIG. 9B shows a plot of rotational speed of the drive shaft versus time for a distal-end-stopping event, for a motor driven system with the shock absorbing element of FIG. 9A.

Referring now to FIG. 9B, a time versus distal end torque diagram may be reviewed. As shown, at the left side of the graph, the drive shaft 20 may be spinning and the torque at the distal end of the drive shaft 20 may be negligible. That is, while some resistance to tip spinning may be present, for our purposes, we may assume that the steady state condition provides a tip resistance that is approximately zero.

When the tip of the drive shaft 20 comes to an abrupt stop the torque applied to the distal end of the drive shaft 20 may begin to increase. That is, assuming that an interrupter is not immediately activated to interrupt the motor rotation, the motor 30 may continue to rotate when the distal end of the drive shaft 20 stops. This additional torque created due to the non-rotating distal tip and the rotating motor 30 may cause the torque at the distal end of the drive shaft to increase. That is, the rotating motor 30 may continue to act on the shock absorbing element 240, which, although it may give slightly, will also transfer some of the additional torque through to the drive shaft 20. As the motor 30 continues to rotate, additional torque may be applied to the shock absorbing element 240, which may absorb some of the torque, but may also transfer some additional torque to the drive shaft 20. The result is that the shock absorbed torque at the distal end of the drive shaft 20 may be lower and take longer to reach than the inertial torque shown in dashed lines in FIG. 9B. That is, in the non-shock absorbed condition, the motor 30 may rotate until the drive shaft 20 reaches its fully wound unresilient condition causing the motor 30 to come to a stop in a short amount of time and causing the full torque of the motor in addition to its loss of momentum to be transferred through the drive shaft 20. In contrast, the shock absorbing embodiments (see FIGS. 8D, 10-13) provide more time for the motor 30 to come to a stop because the shock absorbers 240 allow the motor 30 to rotate through a larger amount of rotation before coming to a stop. Since the torque due to the momentum of the motor 30 is dependent on how abruptly the motor 30 stops, this shock absorbing effect reduces the peak torque. As such, if the motor is uninterrupted, the final torque at the distal tip may be as high as the torque applied by the motor 30, but the torque at the peak may be only slightly higher than the applied torque.

Referring now to FIG. 10A, a first embodiment of a shock absorbing system may be shown. As shown, the motor 30 may include a rotating drive 242 that is rotationally coupled to a drive gear 244. The drive gear 244 may be rotationally engaged with a take-off gear 246 that may be keyed or otherwise coupled to the drive shaft 20 such that rotation of the take-off gear 246 imparts rotation on the drive shaft 20 of the atherectomy device. Accordingly, the motor 30 may be directly geared to the drive shaft 20 and a slip clutch may be omitted. However, as shown, the drive gear 244 may be a shock absorbing drive gear 244 such that resistance to rotation at the drive shaft 20 may be absorbed slightly by the drive gear 244 before increasing the torque in the drive shaft 20 due to motor rotation.

Figure 10B:
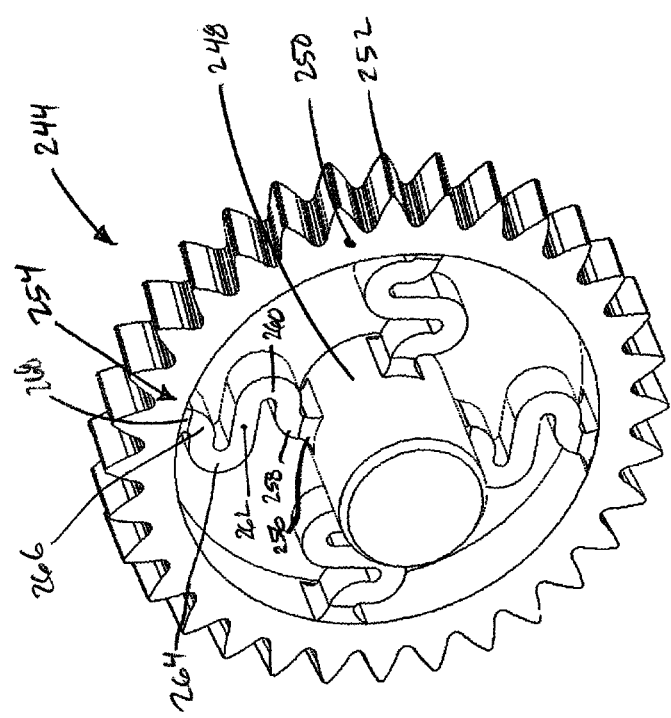
FIG. 10B shows a close-up view of the drive gear of FIG. 9B, according to some embodiments.

As shown in more detail in FIG. 10B, the drive gear 244 may include an internal hub 248 for securing to the rotating drive 242 of the motor 30. The gear 244 may also include a peripheral ring 250 having a plurality of teeth 252 selected together with the tooth count on the take-off gear 246 to provide a suitable gear ratio and allowing for an efficient motor speed relative to drive shaft speed. The hub 248 of the drive gear 244 may be secured to the peripheral ring 250 of the drive gear 244 with a resilient or shock absorbing system. That is, for example, as shown, the shock absorbing system may include a plurality of radially extending elements 254 extending generally radially outward from the hub 248 to an inner surface of the peripheral ring 250. In the present embodiment, the radially extending elements 254 may be substantially S-shaped and there may be four of these shapes. Still other shapes and numbers of radially extending elements 254 may be provided. For example, a series of spokes, struts, or a substantially flat diaphragm may be provided. Still other resilient shock absorbing elements may be provided for resiliently connecting the hub 248 to the peripheral ring 250.

In some embodiments, the drive gear 244 may be a molded product that may be tuned by adjusting and/or changing the molded geometry. In other embodiments, the shock absorbing portion of the gear 244 may be a separate component and tuning or adjusting the resiliency of the system may involve removing and replacing the shock absorbing portion with one of higher or lower resiliency.

The S-shaped portion of the radially extending elements 254 may have a base 256 having an axis extending substantially directly radially outward from the hub 248. The S-shaped portion may include a bent portion 258 turning approximately 90 degrees from the base 256 and then an approximately 180 degree U-turn portion 260 may be provided. A central crossing member 202 may return across the shape slightly past the base 256 to another U-turn portion 264. An additional 90 degree portion 266 may be provided and an opposing base 268 on the inside surface of the peripheral ring 250 may be provided that is substantially radially aligned with the corresponding base 256 on the hub 248. It is to be appreciated that while a particular shape for the radially extending portion 254 has been described, still other geometries for the radially extending portion 254 may be provided.

As can be appreciated, the resilient radially extending portions 254 of the drive 244 gear may deflect under load allowing the hub 248 to rotate relative to the peripheral ring 250 thereby increasing the rotation allowed for the motor 30 in a stoppage condition. This increased rotation may extend the time and distance over which the motor 30 is drawn to a stop thereby reducing the amount of inertial torque transmitted to the drive shaft 20 due to the stoppage.

Referring now to FIG. 11A, another embodiment of a shock absorbing system is shown. In this embodiment, similar to that of FIG. 10A, a motor 30 includes a rotating drive 242 coupled to a drive gear 270. The drive gear is engaged with a take-off gear 272. However, unlike the embodiment of FIG. 10A, the present take-off gear 242 might not be keyed to the drive shaft 20, but may, instead be coupled to the drive shaft 20 with a resilient or shock absorbing element 274. As such, resistance to rotation experienced by the drive shaft 20 may be absorbed slightly by the shock absorbing element 274 when the rotation of the motor 30 attempts to increase the torque in the drive shaft 20.

Figure 11B:
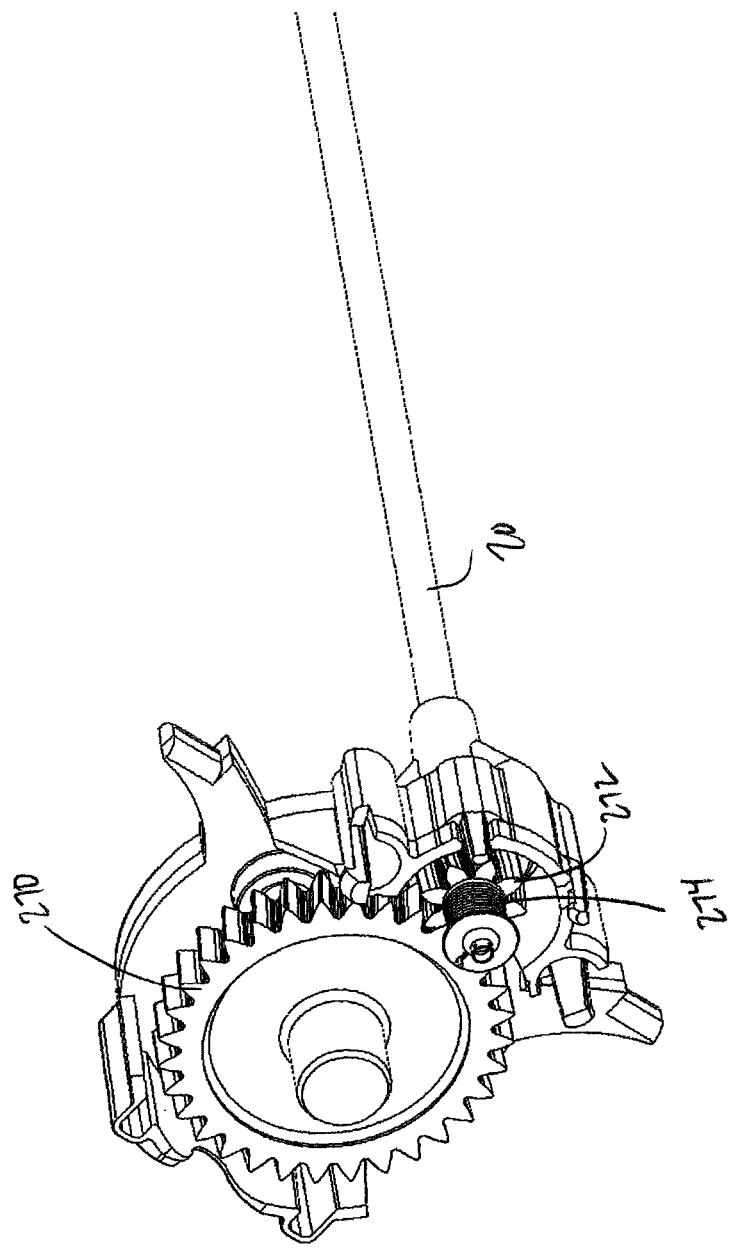
FIG. 11B shows a close-up view of the take-off element of FIG. 10A, according to some embodiments.

As shown in more detail in FIG. 11B, the take-off gear 272 may be arranged concentrically on the drive shaft 20, for example, but may be free to rotate relative to the drive shaft 20. However, one face of the take-off gear 272 may be engaged with one end of a resilient member 274 such as a coil, spring, or other biasing mechanism. The transition between the take-off gear 272 and the resilient member 274 may include a washer plate, for example. The resilient member 274 may be position around the drive shaft 20 and may extend away from the take-off gear 272 to a free end. At the free end of the resilient member opposite the take-off gear 272 a coupling element such as another washer plate may secure the drive shaft to this opposite end. The two ends of the resilient member 274 may be welded, keyed, pinned, or threaded through for example, or otherwise fixed to the take-off gear 272 and the drive shaft 20. As such, rotation of the take-off gear 272 due to the drive gear 270 may cause rotation of the resilient member 274 thereby causing rotation of the drive shaft 20. However, where the drive shaft 20 experiences resistance to rotation, the resilient member 274 may absorb some of the torque of the motor 30 before transferring such torque to the drive shaft 20. As such, the impact of the inertial force on the drive shaft 20 due to the rotating motor 30 may be reduced. It is to be appreciated that while a resilient member 274 in this embodiment has been described as a coil or spring, the resilient member 274 may include a resilient cylindrical bushing made of a resilient material, a mesh material or another material allowing for the torque transfer between the take-off gear 272 and the drive shaft 20 to be controlled.

Figure 12A:
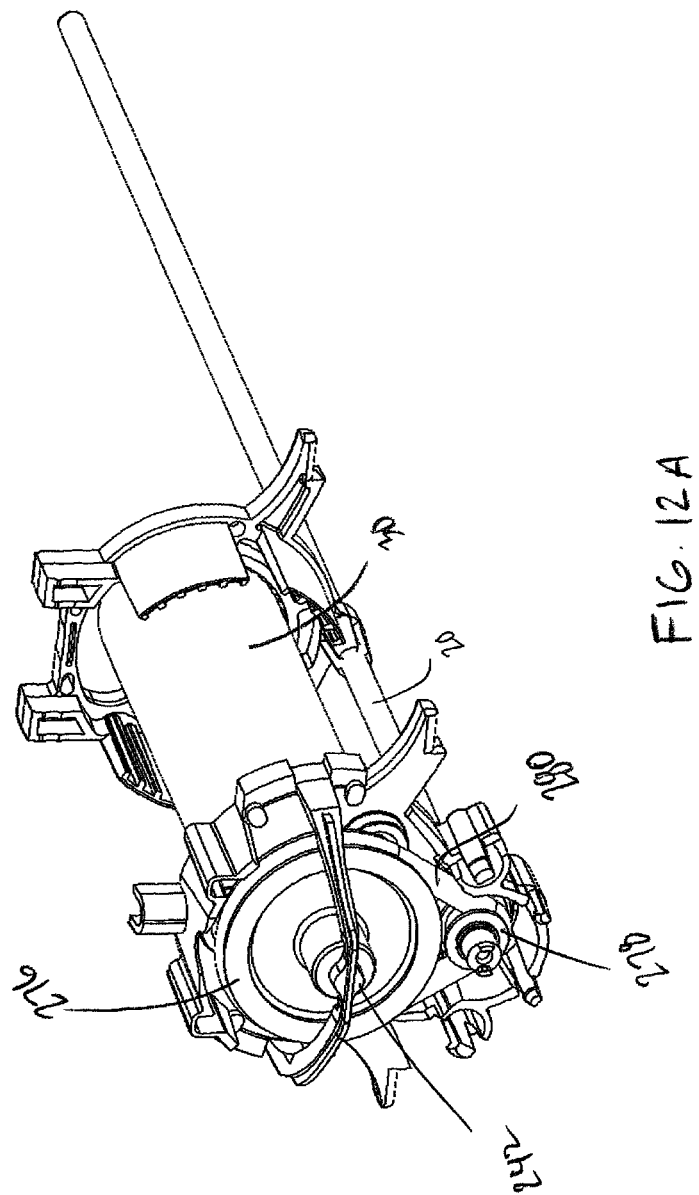
FIG. 12A shows a motor diagram of an atherectomy device having a shock absorbing drive belt, according to some embodiments.

Referring now to FIG. 12A, yet another shock absorbing device may be provided. In this embodiment, unlike the embodiments of FIGS. 10A and 11A, the present embodiment may be a belt-drive system. As such, the system may include a motor 30 having a rotating drive 242. The rotating drive 242 may have a drive pulley 276 arranged thereon and keyed thereto to or otherwise coupled to transfer rotational motion between the rotating drive 242 and the pulley 276. The system may also include a take-off pulley 278 arranged generally in plane with the drive pulley 276 and rotationally coupled to the drive shaft 20. In this embodiment, the drive pulley 276 may be rotationally coupled to the take-off pulley 278 with a resilient belt 280.

Figure 12B:
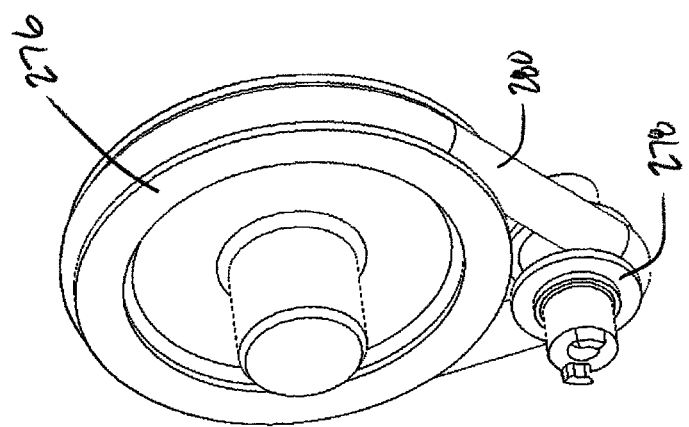
FIG. 12B shows a close-up view of the drive belt of FIG. 11A, according to some embodiments.

In more detail in FIG. 12B, the belt 280 may be arranged to extend around the drive pulley 276 and the take-off pulley 278. The belt 280 may be arranged relatively tightly on the two pulleys 276, 278 thereby transferring torques from the motor 30 to the drive shaft 20 based on the friction of the belt 280 on the surface of each pulley. It is to be appreciated that when the drive pulley 276 is rotating, for example, clockwise in FIG. 12B, the left side of the belt 280 may be in a higher level of tension than the right side stemming from any resistance to rotation that may be present in the drive shaft 20 or other downstream portion of the system. When the drive shaft 20 encounters resistance to rotation, the resilient belt 280 may stretch on the higher tension side of the system and tension on the other side of the system may be slightly relieved due to the increase in differential torque. As such, the belt 280 may be effective to absorb some of the torque from the motor 30 when the drive shaft 20 encounters resistance to rotation. It is to be appreciated that several different belt profiles or cross-sections may be provided. In some embodiments, a round belt, a triangular belt, a rectangular belt, a trapezoidal belt, or other shaped cross-section may be provided. In some embodiments, the cross-sectional shape of the belt 280 may be particularly selected due to its ability to absorb differential toque by deforming based on internal shear forces.

Figure 13A:
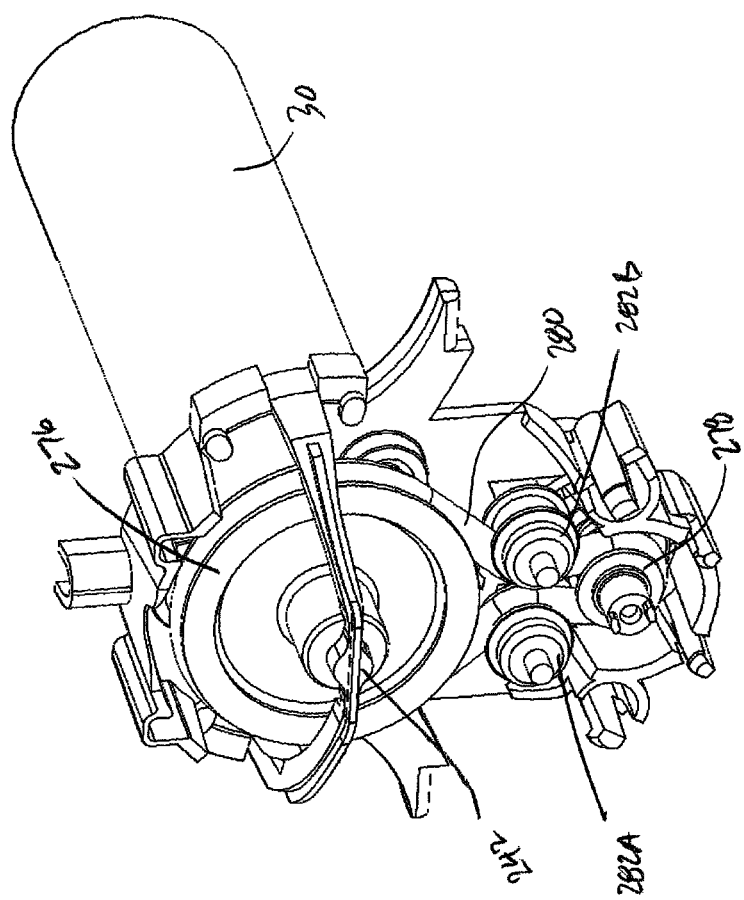
FIG. 13A shows a motor diagram of an atherectomy device having a shock absorbing drive belt and idler system, according to some embodiments.

Referring now to FIG. 13A, yet another embodiment of a shock absorbing device may be provided. In this embodiment, like the embodiment of FIG. 12A, the system may be a belt-driven system. However, it will be appreciated that this particular system could be chain driven or otherwise driven with a more rigid-type belt. In this embodiment, the rotating drive 242 of the motor 30 may include a drive pulley 276 that is rotationally coupled to a take-off pulley 278 on the drive shaft 20 with a belt 280, for example. However, an additional idler pulley may be provided and, as shown, two idler pulleys 282A, 282B may be provided. Like the system of FIG. 12A/12B, the present system may rely on the belt to absorb some of the differential torque, however, the idler pulleys 282A, 282B may also be resilient allowing for more control over the level of shock absorption in the system.

Referring to the more detailed view of FIG. 13B, the several pulleys and a belt are shown. As shown, the idler pulleys 272A, 272B may be arranged along and generally close to the tangent line connecting the outer belt surface of the broader diameter drive pulley 276 to the outer belt surface of the smaller take-off pulley 278. The belt 280 may be routed around respective inside surfaces of the idler pulleys 282A, 282B creating a substantially inverted tear shaped belt route. The idler pulleys 282A, 282B may be positioned on resiliently secured center shafts 284A, 284B such that increased tension on one side of the system may draw one of the idler pulleys 282A out of position while a decrease in tension on the opposing side may cause the respective idler pulley 282B to take up any slack occurring in the belt 280. For example, where the belt in FIG. 13B is rotating clockwise about the drive pulley 276 a particular amount of tension may be present in the left portion of the belt 280, while a slightly lesser amount of tension may be present in the right portion of the belt 280. When the drive shaft 20 encounters an obstruction, the resistance to rotation of the drive shaft 20 may increase causing the tension in the left portion of the belt 280 to increase drawing the left idler pulley 282A outward. Similarly, the tension in the right portion of the belt 280 may decrease allowing the right pulley 282B to move inward to take-up any slack. Since the amount of increased tension on the left may be similar to the amount of decreased tension on the right, the two idler pulleys 282A, 282B, in some embodiments, may be arranged on a common frame such that the right pulley moves inward by an amount equal to or similar to the amount that the left pulley moves outward.

The present shock absorbing systems may be advantageous for absorbing relatively high torsional loading without damaging the medical device drive shaft. The device may provide a means for absorbing the loads allowing the shaft and crown to stop rotating without stopping the whole drive system stopping. In the absence of such a system, the drive shaft may otherwise be the shock absorbing element and may need to be considerably stronger than those using the shock absorbing technology. With the shock absorbing technology, the drive shaft may be designed to perform the function of rotating the sanding member or crown, without the added strength due to shock loading. As described, the shock absorbing member may be arranged on the motor side (i.e., like FIGS. 10A/10B), on the drive side of the drive line (i.e., like FIGS. 11A/11B), or the member may be placed between the drive side and the driven side of the drive line (i.e., like FIGS. 12A/12B and 13A/13B).

The description of the invention and its applications as set forth herein is illustrative and is not intended to limit the scope of the invention. Variations and modifications of the embodiments disclosed herein are possible, and practical alternatives to and equivalents of the various elements of the embodiments would be understood to those of ordinary skill in the art upon study of this patent document. These and other variations and modifications of the embodiments disclosed herein may be made without departing from the scope and spirit of the invention.

What is claimed is:
1. A rotational atherectomy system, comprising:
   an elongated, rotatable, flexible drive shaft having a distal end for insertion into a vasculature of a patient and having a proximal end opposite the distal end remaining outside the vasculature of the patient;
   a motor for rotating the drive shaft; and
   a shock absorbing element coupling the motor to the drive shaft, wherein during steady state conditions, the shock absorbing element transfers the full torque from the motor to the drive shaft through a mechanical coupling, wherein the shock absorbing element comprises a resilient drive gear; and wherein during abrupt increases in the differential torque between the motor and the drive shaft, the shock absorbing element absorbs a portion of the increasing torque and maintains a mechanical coupling between the drive shaft and the motor preventing slippage.

2. The system of claim 1, wherein the shock absorbing element has a torsional resistance that changes based on how tightly wound the shock absorbing element is.

3. The system of claim 1, wherein the shock absorbing element is arranged between a two boundary elements.

4. The system of claim 1, wherein the shock absorbing element directly secures the boundary elements to one another.

5. The system of claim 1, wherein the shock absorbing element has a relaxed length substantially equal to the space between the boundary elements.

6. The system of claim 1, further comprising a system for releasing the torque provided by the motor.

7. The system of claim 1, wherein the shock absorbing element is a coil.

8. The system of claim 1, wherein the shock absorbing element is a spring.

9. The system of claim 1, wherein the shock absorbing element is arrange on the motor side of the drive line.

10. The system of claim 1, wherein the resilient drive gear comprises a hub for rotationally coupling to a motor, a peripheral ring for engaging a take-off gear, and a radially extending resilient element resiliently and radially coupling the hub to the peripheral ring.

11. The system of claim 1, wherein the shock absorbing element is arranged on the driven side of the drive line.

12. The system of claim 11, wherein the shock absorbing element is arranged between a take-off gear and a drive shaft.

13. The system of claim 12, wherein the resilient drive gear rotationally and resiliently couples the take-off gear to the drive shaft.

14. The system of claim 1, wherein the shock absorbing element is arranged between the drive side and the driven side of the drive line.

15. The system of claim 14, wherein the shock absorbing element comprises a resilient drive belt coupling a drive pulley to a take-off pulley.

16. The system of claim 14, wherein the shock absorbing element comprises a drive pulley and a take-off pulley.

17. The system of claim 16, wherein the shock absorbing element comprises a resilient drive belt arranged on the drive pulley and the take-off pulley.

18. The system of claim 17, wherein the shock absorbing element comprises an idler pulley.

19. The system of claim 18, wherein the shock absorbing element comprises a pair of resiliently secured idler pullies.

* * * * *